US006492356B1

(12) United States Patent
Peyman et al.

(10) Patent No.: US 6,492,356 B1
(45) Date of Patent: Dec. 10, 2002

(54) ACYLGUANIDINE DERIVATIVES AS INHIBITORS OF BONE RESORPTION AND AS VITRONECTIN RECEPTOR ANTAGONISTS

(75) Inventors: Anuschirwan Peyman, Kelkheim (DE); Jochen Knolle, San Francisco, CA (US); Gerhard Breipohl, Frankfurt (DE); Karl-Heinz Scheunemann, Liederbach (DE); Denis Carniato, Marcoussis (FR); Jean-Francois Gourvest, Claye Souilly (FR); Thomas Gadek, Oakland, CA (US); Robert McDowell, San Francisco, CA (US); Sarah Catherine Bodary, San Bruno, CA (US); Robert Andrew Cuthbertson, North Fitzroy (AU); Napoleane Ferrara, San Francisco, CA (US)

(73) Assignees: Aventis Pharma Deutschland GmbH, Frankfurt am Main (DE); Genentech, Inc., South San Francisco, CA (US)

( * ) Notice: Subject to any disclaimer, the term of this patent is extended or adjusted under 35 U.S.C. 154(b) by 0 days.

(21) Appl. No.: 09/581,915

(22) PCT Filed: Dec. 10, 1998

(86) PCT No.: PCT/EP98/08051

§ 371 (c)(1),
(2), (4) Date: Nov. 2, 2000

(87) PCT Pub. No.: WO99/32457

PCT Pub. Date: Jul. 1, 1999

(30) Foreign Application Priority Data

Dec. 19, 1997 (EP) .............................. 97122520

(51) Int. Cl.$^7$ ...................... A61K 31/55; A61K 31/415; C07D 245/00; C07D 239/02; C07D 233/04
(52) U.S. Cl. ...................... 514/218; 514/275; 514/398; 514/399; 540/470; 544/297; 544/330; 544/335; 548/331.5; 548/347.1; 548/348.1
(58) Field of Search ................................. 514/218, 275, 514/398, 399; 544/330, 297, 335; 548/347.1, 348.1, 331.5; 540/470

(56) References Cited

FOREIGN PATENT DOCUMENTS

WO     97/21726     6/1997
WO     9721726     *   6/1997

* cited by examiner

Primary Examiner—Mukund J. Shah
Assistant Examiner—Sudhaker B. Patel
(74) Attorney, Agent, or Firm—Foley & Lardner

(57) ABSTRACT

The present invention relates to acylguanidine derivatives of formula (I) in which $R^1$, $R^2$, $R^4$, $R^5$, $R^6$, A, m and n have the meanings indicated in the patent claims, their physiologically tolerable salts and their prodrugs. The compounds of formula (I) are valuable pharmaceutical active ingredients. They are vitronectin receptor antagonists and inhibitors of bone resorption by osteoclasts and are suitable, for example, for the therapy or prophylaxis of diseases which are caused at least partially by an undesired extend of bone resorption, for example of osteoporosis. The invention furthermore relates to processes for the preparation of compounds of formula (I), their use, in particular as pharmaceutical active ingredients, and pharmaceutical preparations comprising them.

20 Claims, No Drawings

ACYLGUANIDINE DERIVATIVES AS INHIBITORS OF BONE RESORPTION AND AS VITRONECTIN RECEPTOR ANTAGONISTS

The present invention relates to acylguanidine derivatives of the formula I,

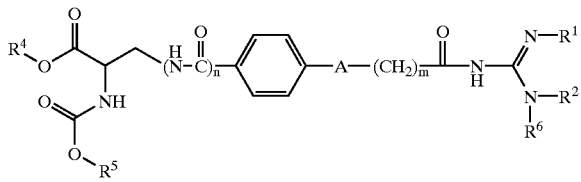

in which $R^1$, $R^2$, $R^4$, $R^5$, $R^6$, A, m and n have the meanings indicated below, their physiologically tolerable salts and their prodrugs. The compounds of the formula I are valuable pharmaceutical active compounds. They are vitronectin receptor antagonists and inhibitors of bone resorption by osteoclasts and are suitable, for example, for the therapy and prophylaxis of diseases which are caused at least partially by an undesired extent of bone resorption, for example of osteoporosis. The invention furthermore relates to processes for the preparation of compounds of the formula I, their use, in particular as pharmaceutical active ingredients, and pharmaceutical preparations comprising them.

Human bones are subject to a constant dynamic renovation process comprising bone resorption and bone formation. These processes are controlled by types of cell specialized for these purposes. Bone resorption is based on the destruction of bone matrix by osteoclasts. The majority of bone disorders are based on a disturbed equilibrium between bone formation and bone resorption.

Osteoporosis is a disease characterized by low bone mass and enhanced bone fragility resulting in an increased risk of fractures. It results from a deficit in new bone formation versus bone resorption during the ongoing remodelling process.

Conventional osteoporosis treatment includes, for example, the administration of bisphosphonates, estrogens, estrogen/progesterone (hormone replacement therapy or HRT), estrogen agonists/antagonists (selective estrogen receptor modulators or SERMs), calcitonin, vitamin D analogues, parathyroid hormone, growth hormone secretagogues, or sodium fluoride (Jardine et al., Annual Reports in Medicinal Chemistry 1996, 31, 211).

Activated osteoclasts are polynuclear cells having a diameter of up to 400 µm, which remove bone matrix Activated osteoclasts become attached to the surface of the bone matrix and secrete proteolytic enzymes and acids into the so-called "sealing zone", the region between their cell membrane and the bone matrix. The acidic environment and the proteases cause the destruction of the bone. The compounds of the formula I inhibit bone resorption by osteoclasts.

Studies have shown that the attachment of osteoclasts to the bones is controlled by integrin receptors on the cell surface of osteoclasts. Integrins are a superfamily of receptors which include, inter alia, the fibrinogen receptor $\alpha_{IIb}\beta_3$ on the blood platelets and the vitronectin receptor $\alpha_v\beta_3$. The vitronectin receptor $\alpha_v\beta_3$ is a membrane glycoprotein which is expressed on the cell surface of a number of cells such as endothelial cells, cells of the vascular smooth musculature, osteoclasts and tumor cells. The vitronectin receptor $\alpha_{IIb}\beta_3$, which is expressed on the osteoclast membrane, controls the process of attachment to the bones and bone resorption and thus contributes to osteoporosis. $\alpha_v\beta_3$ in this case binds to bone matrix proteins such as osteopontin, bone sialoprotein and thrombospontin, which contain the tripeptide motif Arg-Gly-Asp (or RGD).

Horton and coworkers describe RGD peptides and an anti-vitronectin receptor antibody (23C6) Which inhibit tooth destruction by osteoclasts and the migration of osteociasts (Horton et al., Exp. Cell. Res. 1991, 195, 368). In J. Cell Biol. 1990, 111, 1713, Sato et al. describe echistatin, an RGD peptide from snake venom, as a potent inhibitor of bone resorption in a tissue culture and as an inhibitor of osteoclast adhesion to the bones. Fischer et al. (Endocrinology 1993, 132, 1411) were able to show in the rat that echistatin also inhibits bone resorption in vivo.

It was furthermore shown that the vitronectin receptor $\alpha_v\beta_3$ on human cells of the vascular smooth musculature of the aorta stimulates the migration of these cells into the neointima, which finally leads to arteriosclerosis and restenosis after angioplasty (Brown et al., Cardiovascular Res. 1994, 28, 1815). Yue et al. (Pharmacology Reviews and Communications 1998, 10, 9–18) showed the inhibition of neointima formation using an $\alpha_v\beta_3$ antagonist.

Brooks et al. (Cell 1994, 79, 1157) showed that antibodies against $\alpha_v\beta_3$ or $\alpha_v\beta_3$ antagonists can cause a shrinkage of tumors by inducing the apoptosis of blood vessel cells during angiogenesis. The vitronectin receptor $\alpha_v\beta_3$ is also involved in the progression of a variety of other types of cancer, and is overexpressed in malignant melanoma cells (Engleman et al., Annual Reports in Medicinal Chemistry 1996, 31, 191). The melanoma invasiveness correlated with this overexpression (Stracke et al., Encyclopedia of Cancer, volume III, 1855, Academic Press, 1997; Hillis et al., Clinical Science 1996, 91, 639). Carron et al. (Cancer Res. 1998, 58, 1930) describe the inhibition of tumor growth and the inhibition of hypercalcemia of malignancy using an $\alpha_v\beta_3$ antagonist.

Cheresh et al. (Science 1995, 270, 1500) describe anti-$\alpha_{v\beta3}$ antibodies or $\alpha_v\beta_3$ antagonists which inhibit the bFGF-induced angiogenesis processes in the rat eye, a property which can be used therapeutically in the treatment of retinopathies.

Influencing of the vitronectin receptor or of the interactions in which it is involved thus offers the possibility of influencing different disease states for whose therapy and prophylaxis there continues to be a need for suitable pharmaceutical active ingredients.

The patent application WO-A-94/12181 describes substituted aromatic ring systems and WO-A-94/08577 describes substituted heterocycles as fibrinogen receptor antagonists and inhibitors of platelet aggregation. EP-A-528 586 and EP-A-528 587 disclose aminoalkyl-substituted or heterocyclyl-substituted phenylalanine derivatives. WO-A-95/32710 discloses aryl derivatives as inhibitors of bone resorption by osteoclasts. WO-A-96/00574 describes benzodiazepines, and WO-A-96/00730 describes fibrinogen receptor antagonist templates, in particular benzodiazepines which are linked to a nitrogen-bearing 5-membered ring, as vitronectin receptor antagonists. WO-A-97/21726 describes agents for promoting bone formation which belong to various classes of compounds, among them tyrosine derivatives containing an unsubstituted guanidino group. Further investigations have shown that the acylguanidines of the formula I are particularly strong inhibitors of the vitronectin receptor and of bone resorption by osteoclasts.

The present invention relates to compounds of the formula I,

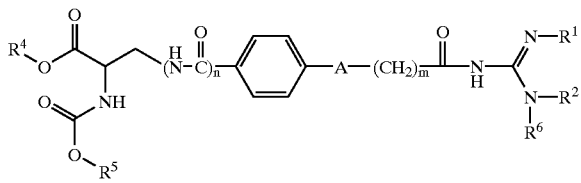

in which
R¹ and R² independently of one another are hydrogen or $(C_1-C_6)$-alkyl which is unsubstituted or substituted by R³, with the proviso that R¹ and R² are not both hydrogen at the same time, or in which the radicals R¹- and R²-together are a saturated or unsaturated bivalent $(C_2-C_9)$-alkylene radical, for example the group —$(CH_2)_p$—, in which p is 2, 3, 4, 5, 6, 7, 8 or 9, which is unsubstituted or is substituted by one or more groups from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$cycloalkyl, $(C_3-C_{12})$-cycloalkyl-$(C_1-C_6)$-alkyl- and oxo, where a 5-membered to 7-membered saturated or unsaturated ring which is unsubstituted or is substituted by R³, in particular by one or two radicals R³, and which is a carbocyclic ring or a heterocyclic ring containing one or two ring nitrogen atoms, can be fused to a carboncarbon bond in the $(C_2-C_9)$-alkylene radical;

R³ is $(C_1-C_8)$-alkyl, $(C_1-C_8)$-alkoxy, $(C_5-C_{14})$-aryl, $(C_5-C_{14})$-aryl-$(C_1-C_4)$-alkyl- halogen, trifluoromethyl, hydroxyl, nitro or amino;

R⁴ is hydrogen, $(C_1-C_6)$-alkyl-CO—O—$(C_1-C_4)$-alkyl- or $(C_1-C_6)$-alkyl, which is unsubstituted or is substituted by a radical from the group consisting of hydroxyl, $(C_1-C_4)$-alkoxy, $(C_1-C_4)$-alkyl-S(O)$_2$—, NR⁷R⁷' and N⁺R⁷R⁷'R⁷''Q⁻, where R⁷, R⁷' and R⁷'' independently of one another are hydrogen, $(C_1-C_6)$-alkyl, $(C_5-C_{14})$-aryl or $(C_5-C_{14})$-aryl-$(C_1-C_6)$-alkyl- and Q⁻ is a physiologically tolerable anion, or in which R⁴ is one of the radicals

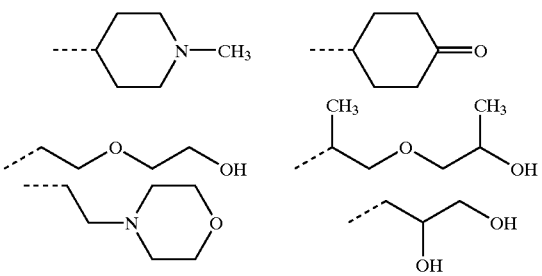

in which the bonds, via which the radicals are bonded, are indicated by dashed lines;

R⁵ is $(C_1-C_8)$-alkyl, $(C_6-C_{14})$-aryl-$(C_{1-6})$-alkyl- or $(C_5-C_{14})$-heteroaryl-$(C_1-C_5)$-alkyl-, where the aryl radical or the heteroaryl radical is unsubstituted or is substituted by one, two or three radicals R³, R⁶ is hydrogen, $(C_1-C_6)$-alkyl-O—CO—, hydroxyl, $(C_1-C_6)$-alkyl-O—CO—O— or nitro;

A is CH$_2$, O, S or NH;

m is 1, 2 or 3;

n is 0 or 1;

in all their stereoisomeric forms and mixtures thereof in all ratios, and their physiologically tolerable salts and their prodrugs.

All radicals which can occur more than once in the compounds of the formula I, for example the radicals R³, can in each case independently of one another have the meanings indicated, and they can in each case be identical or different. Similarly, all radicals of which it is said that they independently of one another can have a meaning indicated, can in each case be identical or different.

The alkyl radicals occurring in the substituents can be straight-chain or branched and can be saturated or mono-unsaturated or poly-unsaturated. This also applies if they carry substituents or occur as substituents of other radicals, for example in alkoxy radicals, alkoxycarbonyl radicals or arylalkyl radicals. The same applies to alkylene radicals (=alkanediyl radicals). Examples of suitable $(C_1-C_9)$-alkyl radicals are methyl, ethyl, propyl, butyl, pentyl, hexyl, heptyl, octyl, nonyl, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Preferred alkyl radicals are methyl, ethyl, n-propyl, isopropyl, n-butyl, isobutyl, sec-butyl and tert-butyl. The bivalent radicals corresponding to the abovementioned monovalent radicals, for example methylene, ethylene, 1,3-propylene, 1,2-propylene (=1-methylethylene), 2,3-butylene (=1,2-dimethylethylene), 1,4-butylene, 1,6-hexylene, are examples of alkylene radicals.

Unsaturated alkyl radicals are, for example, alkenyl radicals such as vinyl, 1-propenyl, allyl, butenyl, 3-methyl-2-butenyl or alkynyl radicals such as ethynyl, 1-propynyl or propargyl. Unsaturated alkylene radicals, that is alkenylene radicals (=alkenediyl radicals) and alkynylene radicals (=alkynediyl radicals), can likewise be straight-chain or branched. Examples of alkenylene radicals are vinylene or propenylene, examples of alkynylene radicals are ethynylene or propynylene.

Cycloalkyl radicals can be, for example, monocyclic, bicyclic or tricyclic. Monocyclic cycloalkyl radicals are, in particular, cyclopropyl, cyclobutyl, cyclopentyl, cyclohexyl, cycloheptyl, cyclooctyl, cyclononyl, cyclodecyl, cycloundecyl or cyclododecyl, which, however, can also be substituted by, for example, $(C_1-C_4)$-alkyl. Examples of substituted cycloalkyl radicals which may be mentioned are 4-methylcyclohexyl and 2,3-dimethylcyclopentyl.

Halogen is, for example, fluorine, chlorine, bromine or iodine.

$(C_5-C_{14})$-Aryl includes heterocyclic $(C_5-C_{14})$-aryl radicals (=$(C_5-C_{14})$-heteroaryl radicals) in which one or more of the 5 to 14 ring carbon atoms are replaced by heteroatoms such as nitrogen, oxygen or sulfur, and carbocyclic $(C_6-C_{14})$-aryl radicals. Examples of carbocyclic $(C_5-C_{14})$-aryl radicals are phenyl, naphthyl, biphenylyl, anthryl or fluorenyl, where 1-naphthyl, 2-naphthyl and in particular phenyl are preferred. If not stated otherwise, aryl radicals, in particular phenyl radicals, can be unsubstituted or substituted by one or more radicals, preferably one, two or three radicals. In particular aryl radicals can be substituted by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, such as fluorine, chlorine and bromine, nitro, amino, trifluoromethyl, hydroxyl, methylenedioxy, cyano, hydroxycarbonyl, aminocarbonyl, $(C_1-C_4)$-alkoxycarbonyl, phenyl, phenoxy, benzyl and benzyloxy. Generally, only up to two nitro groups can occur as substituents in the compounds of the formula I according to the invention.

In monosubstituted phenyl radicals, the substituent can be located in the 2-position, the 3-position or the 4-position, the 3- and the 4-position being preferred. If phenyl is disubstituted, the substituents can be in the 2,3-position, 2,4-position, 2,5-position, 2,6-position, 3,4-position or 3,5-position. Preferably, in disubstituted phenyl radicals, the two substituents are arranged in the 3,4-position, relative to the linkage site. In trisubstituted phenyl radicals, the substituents can be in the 2,3,4-position, 2,3,5-position, 2,3,6-position, 2,4,5-position, 2,4,6-position or 3,4,5-position.

Beside carbocyclic systems, $(C_5-C_{14})$-aryl groups can also be monocyclic or polycyclic aromatic ring systems in which 1, 2, 3, 4 or 5 of the 5 to 14 ring carbon atoms are replaced by heteroatoms, in particular by identical or different heteroatoms from the group consisting of nitrogen, oxygen and sulfur. Examples of heterocyclic $(C_5-C_{14})$-aryl groups and $(C_5-C_{14})$-heteroaryl groups are 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl, or benzo-fused, cyclopenta-, cyclohexa- or cyclohepta-fused derivatives of these radicals. The heterocyclic systems can be substituted by the same substituents as the abovementioned carbocyclic aryl systems.

In the series of these heteroaryl groups, monocyclic or bicyclic aromatic ring systems having 1, 2 or 3 heteroatoms, in particular having 1 or 2 heteroatoms, from the group consisting of N, O, S, which can be unsubstituted or substituted by 1, 2 or 3 substituents from the group consisting of $(C_1-C_6)$-alkyl, $(C_1-C_6)$-alkoxy, fluorine, chlorine, nitro, amino, trifluoromethyl, hydroxyl, $(C_1-C_4)$-alkoxycarbonyl, phenyl, phenoxy, benzyloxy and benzyl, are preferred. Particularly preferred here are monocyclic or bicyclic aromatic 5-membered to 10-membered ring systems having 1 to 3 heteroatoms, in particular having 1 or 2 heteroatoms, from the group consisting of N, O, S, which can be substituted by 1 to 2 substituents from the group consisting of $(C_1-C_4)$-alkyl, $(C_1-C_4)$-alkoxy, phenyl, phenoxy, benzyl and benzyloxy.

If the two radicals $R^1$- and $R^2$- together represent a bivalent saturated or unsaturated $(C_2-C_9)$-alkylene radical, these two radicals, together with the two nitrogen atoms to which they are bonded, and the central carbon atom of the guanidino group to which these two nitrogen atoms are bonded, form a monocyclic 1,3-diazaheterocycle which is bonded to the nitrogen atom in the group $(CH_2)_m$—CO—NH via its 2-position. Examples of radicals of such 1,3-diazaheterocycles which can be substituted as indicated in the $(C_2-C_9)$-alkylene radical and also on the guanidino nitrogen atom, are the 1H-imidazol-2-yl radical, the 4,5-dihydro-1H-imidazol-2-yl radical, the 1,4,5,6-tetrahydro-pyrimidin-2-yl radical or the 4,5,6,7-tetrahydro-1H-1,3-diazepin-2-yl radical. If a 5-membered to 7-membered ring is fused to a carbon-carbon bond in the $(C_2-C_9)$-alkylene radical, then the two radicals $R^1$ and $R^2$, together with the two nitrogen atoms to which they are bonded, and the central carbon atom of the guanidino group to which these two nitrogen atoms are bonded, form a bicyclic heterocycle which is bonded to the nitrogen atom in the group $(CH_2)_m$—CO—NH and which can be substituted as indicated. The fused (or condensed) 5-membered to 7-membered ring can be saturated, mono-unsaturated or di-unsaturated or aromatic. Thus, for example, a cyclopentane ring, cyclohexane ring, cyclohexene ring, cyclohexadiene ring, cycloheptane ring or benzene ring can be condensed. Examples of radicals of such bicyclic heterocycles which can be bonded to the nitrogen atom in the group $(CH_2)_m$—CO—NH are the 1,3a,4,5,6,6a-hexahydro-1,3-diazapentalen-2-yl radical, the 1H-benzimidazol-2-yl radical, the 3a,4,5,6,7,7a-hexahydro-1H-benzimidazol-2-yl radical, the 4,5,6,7-tetrahydro-1H-benzimidazol-2-yl radical, the 4,7-dihydro-1H-benzimidazol-2-yl radical or the 1H-imidazo[4,5-b]pyridin-2-yl radical. If a condensed ring is substituted and/or if the $(C_2-C_5)$-akylene radical is substituted, they are preferably independently of one another monosubstituted or disubstituted by identical or different radicals $R^3$. If alkyl groups representing $R^1$ and/or $R^2$ are substituted, they are preferably independently of one another monosubstituted or disubstituted, in particular monosubstituted, by identical or different radicals $R^3$.

Optically active carbon atoms contained in the compounds of the formula I can independently of one another have the R configuration or the S configuration. The configurations on different centers can be identical or different. The compounds of the formula I can be present in the form of pure enantiomers or pure diastereomers or in the form of enantiomer mixtures, for example in the form of racemates, or of diastereomer mixtures. The present invention relates to both pure enantiomers and enantiomer mixtures, for example racemates, and diastereomers and diastereomer mixtures. The invention comprises mixtures of two or of more than two stereoisomers of the formula I and all ratios of the stereoisomers in the mixtures. The compounds of the formula I can optionally be present as E isomers or Z isomers. The invention relates to both pure E isomers and pure Z isomers and E/Z mixtures in all ratios. The invention also comprises all tautomeric forms of the compounds of the formula I. For example, beside the form shown in the formula I, also the form in which the acylguanidine units is present as a —CO—N=C(NHR$^1$)—NR$^2$R$^6$ group, and all other forms which differ by different positions of mobile hydrogen atoms are comprised. Diastereomers, including E/Z isomers, can be separated into the individual isomers, for example, by chromatography. Racemates can be separated into the two enantiomers by customary methods, for example, by chromatography on chiral phases or by resolution. Stereochemically uniform compounds can also be obtained by employing stereochemically uniform starting compounds or by using stereoselective reactions.

Physiologically tolerable salts of the compounds of formula I are nontoxic, physiologically acceptable, in particular pharmaceutically utilizable, salts. Such salts of compounds of the formula I which contain acidic groups, for example carboxylic acid groups, are, for example, alkali metal salts or alkaline earth metal salts, such as, for example, sodium salts, potassium salts, magnesium salts and calcium salts, and also salts with physiologically tolerable quaternary ammonium ions and acid addition salts with ammonia and physiologically tolerable organic amines, such as, for example, triethylamine, ethanolamine or tris-2-hydroxyethyl)amine. Compounds of the formula I which contain basic groups, form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds of the formula I which contain a basic group and an acidic group, for example the guanidino group and a carboxyl group, can be present as zwitterions (betaines), which are likewise included by the present invention.

The physiologically tolerable anion $Q^-$, which is contained in the compounds of the formula I when $R^4$ is an alkyl radical which is substituted by a positively charged ammonium group, is, in particular, a monovalent anion or an eqivalent of a polyvalent anion of a nontoxic, physiologically acceptable, in particular also pharmaceutically utilizable, inorganic or organic acid, for example the anion or an anion equivalent of one of the abovementioned acids suitable for the formation of acid addition salts. Q⁻ can thus be, for example, one of the anions (or an anion equivalent) chloride, sulfate, phosphate, acetate, citrate, benzoate, maleate, fumarate, tartrate, methanesulfonate or p-toluenesulfonate.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals, but are suitable, for example, as intermediates for carrying out other chemical modifications of the compounds of the formula I or as starting materials for the preparation of physiologically tolerable salts.

The present invention moreover includes all solvates of compounds of the formula I, for example hydrates or adducts with alcohols, and also derivatives of the compounds of the formula I, for example esters and other prodrugs and other physiologically tolerable derivatives, as well as active metabolites of the compounds of the formula I. The invention relates in particular to prodrugs of the compounds of the formula I, which can be converted into compounds of the formula I under physiological conditions. Suitable prodrugs for the compounds of the formula I, i.e. chemically modified derivatives of the compounds of the formula I having properties which are improved in a desired manner, are known to those skilled in the art. More detailed information relating to prodrugs is found, for example, in Fleisher et al., Advanced Drug Delivery Reviews 19 (1996) 115–130; Design of Prodrugs, H. Bundgaard, Ed., Elsevier, 1985; H. Bundgaard, Drugs of the Future 16 (1991) 443; Saulnier et al., Bioorg. Med. Chem. Lett. 4 (1994) 1985; Safadi et al., Pharmaceutical Res. 10 (1993) 1350. Suitable prodrugs for the compounds of the formula I are especially ester prodrugs, for example $(C_1–C_4)$-alkyl esters, of carboxylic acid groups, in particular of the COOH group, which is present when $R^4$ in the group $COOR^4$ is hydrogen, and also acyl prodrugs and carbamate prodrugs of acylatable a nitrogen-containing groups such as amino groups and in particular the guanidino group. In the acyl prodrugs or carbamate prodrugs, one or more times, for example twice, a hydrogen atom located on a nitrogen atom in these groups is replaced by an acyl group or carbamate group. Suitable acyl groups and carbamate groups for the acyl prodrugs and carbamate prodrugs are, for example, the groups $R^{10}$—CO— and $R^{11}$O—CO—, in which $R^{10}$ is hydrogen, $(C_1–C_{18})$-alkyl, $(C_3–C_{14})$-cycloalkyl, $(C_3–C_{14})$-cycloalkyl-$(C^1–C_8)$-alkyl-, $(C^5–C_{14})$-aryl, in which 1 to 5 carbon atoms can be replaced by heteroatoms such as N, O, S, or $(C_5–C_{14})$-aryl-$(C_1–C_8)$-aryl-, in which 1 to 5 carbon atoms in the aryl moiety can be replaced by heteroatoms such as N, O, S, and $R^{11}$ has the meanings indicated for $R^{10}$ with the exception of hydrogen.

In the compounds of the formula I, the radicals $R^1$ and $R^2$ preferably together are a saturated or unsaturated, in particular a saturated, bivalent $(C_2–C_5)$-alkylene radical, in particular a $(C_2–C_4)$-alkylene radical, especially a $(C_2–C_3)$-alkylene radical, which is unsubstituted or is substituted by one or two identical or different radicals from the group consisting of halogen, $(C_1–C_6)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo, where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms can be fused to a carboncarbon bond in the alkylene radical. In the compounds of the formula I, the radicals $R^1$ and $R^2$ are particularly preferably the group —$(CH_2)_p$—, in which p is the numbers 2, 3, 4 or 5, preferably the numbers 2, 3 or 4, particularly preferably the numbers 2 or 3, and which is unsubstituted or is substituted by one or two identical or different radicals from the group consisting of halogen, $(C_1–C_6)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-,$(C_3–C_{12})$-cycloalkyl, $(C_3–C_{12})$-cycloalkyl-$(C_1–C_6)$-alkyl- and oxo, where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carbon-carbon bond in the group —$(CH_2)_p$—.

$R^3$ is preferably $(C_1–C_4)$-alkyl or $(C_1–C_4)$-alkoxy.

$R^4$ is preferably hydrogen or unsubstituted or substituted $(C_1–C_6)$-alkyl, particularly preferably hydrogen or $(C_1–C_6)$-alkyl, which is unsubstituted or substituted by a radical from the group consisting of $(C_1–C_4)$-alkoxy, $(C_1–C_4)$-alkyl-$S(O)_2$— and $NR^7R^{7'}$, where $R^7$ and $R^{7'}$ independently of one another are hydrogen or $(C_1–C_4)$-alkyl. $R^4$ is very particularly preferably hydrogen or unsubstituted or substituted $(C_1–C_4)$-alkyl, especially preferably hydrogen or $(C_1–C_4)$-alkyl which is unsubstituted or substituted by a radical from the group consisting of $(C_1–C_4)$-alkoxy, $(C_1–C_4)$-alkyl-$S(O)_2$— and $NR^7R^{7'}$, where $R^7$ and $R^{7'}$ independently of one another are hydrogen or $(C_1–C_4)$-alkyl.

$R^5$ is preferably $(C_1–C_8)$-alkyl or a radical of the formula II

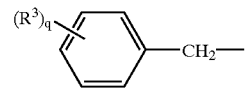

II in which the radicals $R^3$ can be identical or different and can be located in any desired positions of the phenyl radical, where q is 0, 1 or 2, preferably 0 or 1, particularly preferably 0. $R^5$ is particularly preferably $(C_1–C_4)$-alkyl or the radical of the formula II, in which q is 0 or 1, very particularly preferably $R^5$ is the radical of the formula II, in which q is 0 or 1, i.e. an unsubstituted benzyl radical or a benzyl radical monosubstituted in the ortho-position, meta-position or paraposition by $R^3$.

$R^6$ is preferably hydrogen or $(C_1–C_6)$-alkyl-O—CO—, particularly preferably hydrogen or $(C_1–C_4)$-alkyl-O—CO—, in particular hydrogen.

A is preferably $CH_2$ or O.

Preferred compounds of the formula I are those compounds in which one or more of the radicals have preferred meanings or one specific of the preferred meanings, all combinations of such preferred meanings being a subject of the present invention. Particularly preferred compounds of the formula I are those compounds in which $R^1$ and $R^2$ together are a saturated or unsaturated bivalent $(C_2-C_5)$-alkylene radical, in particular together the group —$(CH_2)_p$—, in which p is the numbers 2, 3, 4 or 5, where the $(C_2-C_5)$-alkylene radical and the group —$(CH_2)_p$— are unsubstituted or are substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_4)$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, and where a 5-membered to 7-membered saturated or unsaturated ring which is unsubstituted or substituted by $R^3$, in particular by one or two radicals $R^3$, and which is a carbocyclic ring or heterocyclic ring containing one or two ring nitrogen atoms, can be fused to a carbon-carbon bond in the $(C_2-C_5)$-alkylene radical and in the group —$(CH_2)_p$—;

$R^3$ is $(C_1-C_4)$-alkyl or $(C_1-C_4)$-alkoxy;

$R^4$ is hydrogen or $C_1-C_6$-alkyl which is unsubstituted or is substituted by a radical from the group consisting of $(C_1-C_4)$-alkoxy, $C_1-C_4$-alkyl-$S(O)_2$— and $NR^7R^{7'}$, where $R^7$ and $R^{7'}$ independently of one another are hydrogen or $C_1-C_4$-alkyl;

$R^5$ is $(C_1-C_8)$-alkyl or a radical of the formula II

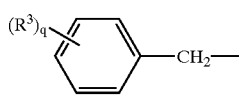

II in which q is 0 or 1 and the radical $R^3$ can be located in any desired position of the phenyl radical;

$R^6$ is hydrogen or $(C_1-C_6)$-alkyl-O—CO—;

A is $CH_2$ or O;

m is 1, 2 or 3;

n is 0 or 1;

in all their stereoisomeric forms and mixtures thereof in all ratios, and their physiologically tolerable salts and their prodrugs.

Very particularly preferred compounds of the formula I are those compounds in which $R^1$ and $R^2$ together are a saturated or unsaturated bivalent $(C_2-C_4)$-alkylene radical, in particular together the group —$(CH_2)_p$—, in which p is the numbers 2, 3 or 4, where the $(C_2-C_4)$-alkylene radical and the group —$(CH_2)_p$— are unsubstituted or are substituted by a radical from the group consisting of halogen, $(C_1-C_6)$-alkyl, $(C_1-C_6)$-alkoxy, $(C_6-C_{14})$aryl, $(C_6-C_4)$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_2)$-cycloalkyl, $(C_3-C_{12})$-cycloalkyl-$(C_1-C_6)$-alkyl- and oxo, and where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carboncarbon bond in the $(C_2-C_4)$-alkylene radical and in the group —$(CH_2)_p$—;

$R^3$ is $(C_1-C_4)$-alkyl or $(C_1-C_4)$-alkoxy;

$R^4$ is hydrogen or $(C_1-C_6)$-alkyl;

$R^5$ is $(C_1-C_4)$-alkyl or a radical of the formula II

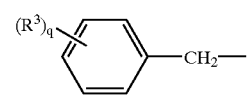

II in which q is 0 or 1 and the radical $R^3$ can be located in any desired position of the phenyl radical;

$R^6$ is hydrogen or $(C_1-C_4)$-alkyl-O—CO—;

A is $CH_2$ or O;

m is 1, 2 or 3;

n is 0 or 1;

in all their stereoisomeric forms and mixtures thereof in all ratios, and their physiologically tolerable salts and their prodrugs.

Especially preferred compounds of the formula I are those in which:

$R^1$ and $R^2$ together are a saturated or unsaturated bivalent $(C_2-C_3)$-alkylene radical, in particular together the group —$(CH_2)_p$—, in which p is the numbers 2 or 3, where the $(C_2-C_3)$-alkylene radical and the group —$(CH_2)_p$— are unsubstituted or are substituted by a radical from the group consisting of halogen, $(C_1-C_6)$-alkyl, $(C_1-C_6)$-alkoxy, $(C_6-C_{14})$-aryl, $(C_6-C_4)$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, and where a 5-remembered to 7-membered saturated or unsaturated ring which is unsubstituted or is substituted by $R^3_1$, in particular by one or two radicals $R^3$, and which is a carbocyclic ring or heterocyclic ring containing one or two ring nitrogen atoms, can be fused to a carbon-carbon bond in the $(C_2-C_3)$-alkylene radical and in the group —$(CH_2)_p$—;

$R^3$ is $(C_1-C_4)$-alkyl or $(C_1-C_4)$-alkoxy;

$R^4$ is hydrogen or $(C_1-C_4)$-alkyl;

$R^5$ is $(C_1-C_4)$-alkyl or a radical of the formula II

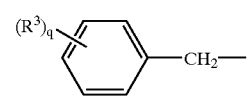

II in which q is 0 or 1 and the radical $R^3$ can be located in any desired position of the phenyl radical;

$R^6$ is hydrogen or $(C_1-C_4)$-alkyl-O—CO—;

A is $CH_2$;

m is 1;

n is 1;

in all their stereoisomeric forms and mixtures thereof in all ratios, and their physiologically tolerable salts and their prodrugs.

Especially preferred compounds of the formula I are also those in which $R^1$ and $R^2$ together are a saturated or unsaturated bivalent $(C_2-C_3)$-alkylene radical, in particular together the group —$(CH_2)_p$—, in which p is the numbers 2 or 3, where the $(C_2-C_3)$-alkylene radical and the group —$(CH_2)_p$— are unsubstituted or are substituted by a radical from the group consisting of halogen, $C_1-C_6$-alkyl, $C_1-C_6$-alkoxy, $(C_6-C_{14})$-aryl, $(C_6-C_4)$-aryl-$(C_1-C_6)$-alkyl-, $(C_5-C_{14})$-heteroaryl, $(C_5-C_{14})$- heteroaryl-$(C_1-C_6)$-alkyl-, $(C_3-C_{12})$-cloalkyl, $(C_3-C_{12})$-cycloalkyl-$(C_1-C_6)$-alkyl- and oxo, and where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carboncarbon bond in the $(C_2-C_3)$-alkylene radical and in the group —$(CH_2)_p$—;

$R^3$ is $(C_1-C_4)$-alkyl or $(C_1-C_4)$-alkoxy;

$R^4$ is hydrogen or $(C_1-C_4)$-alkyl;

$R^5$ is $(C_1-C_4)$-alkyl or a radical of the formula II

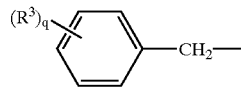

II in which q is 0 or 1 and the radical $R^3$ can be located in any desired position of the phenyl radical;

$R^6$ is hydrogen or $C_1-C_4$-alkyl-O—CO—;

A is oxygen;

m is 1;

n is 1;

in all their stereoisomeric forms and mixtures thereof in all ratios, and their physiologically tolerable salts and their prodrugs.

Especially preferred compounds of the formula I are furthermore those in which $R^1$ and $R^2$ together are a saturated or unsaturated bivalent $(C_2-C_3)$-alkylene radical, in particular together the group —$(CH_2)_p$—, in which p is the numbers 2 or 3, where the $(C_2-C_3)$-alkylene radical and the group —$(CH_2)_p$— are unsubstituted or are substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$ alkyl- and oxo, and where a 5-membered to 7-membered saturated or unsaturated ring which is unsubstituted or is substituted by $R^3$, in particular by one or two radicals $R^3$, and which is a carbocyclic ring or heterocyclic ring containing one or two ring nitrogen atoms, can be fused to a carboncarbon bond in the $(C_2-C_3)$-alkylene radical and in the group —$(CH_2)_p$—;

$R^3$ is $C_1-C_4$-alkyl or $(C_1-C_4)$-alkoxy;

$R^4$ is hydrogen or $C_1-C_4$-alkyl;

$R^5$ is $C_1-C_4$-alkyl or a radical of the formula II

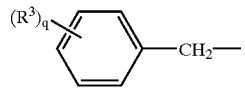

II in which q is 0 or 1 and the radical $R^3$ can be located in any desired position of the phenyl radical;

$R^6$ is hydrogen or $C_1-C_4$-alkyl-O—CO—;

A is oxygen;

m is 3;

n is 0;

in all their stereoisomeric forms and mixtures thereof in all ratios, and their physiologically tolerable salts and their prodrugs.

Particularly especially preferred compounds of the formula I are those in which $R^1$ and $R^2$ together are a saturated bivalent $(C_2-C_3)$-alkylene radical which is unsubstituted, in particular together are the unsubstituted group —$(CH_2)_2$— or the unsubstituted group —$(CH_2)_3$—;

$R^4$ is hydrogen or $(C_1-C_4)$-alkyl;

$R^5$ is unsubstituted benzyl;

$R^6$ is hydrogen;

A is oxygen;

m is 3;

n is 0;

in all their stereoisomeric forms and mixtures thereof in all ratios, and their physiologically tolerable salts and their prodrugs.

Preferred compounds of the formula I are additionally those in which the carbon atom to which the two groups $R^4O$—CO— and $R^5OCO$—NH— are bonded has the S configuration.

The present invention also relates to processes for the preparation of the compounds of the formula I. The compounds can generally be prepared, for example in the course of a convergent synthesis, by linkage of two or more fragments which can be derived retrosynthetically from the formula I. In the preparation of the compounds of the formula I it can generally be advantageous or necessary in the course of the synthesis to introduce functional groups which could lead to undesired reactions or side reactions in the respective synthesis step, in the form of precursors which are later converted into the desired functional groups, or temporarily to block functional groups by a protective group strategy suited to the synthesis problem, which is known to those skilled in the art (Greene and Wuts, Protective Groups in Organic Synthesis, Wiley, 1991).

Thus the compounds of the formula I can be prepared, for example, by linking in a manner known per se a carboxylic acid or carboxylic acid derivative of the

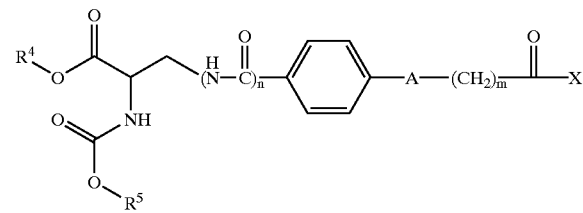

III in which $R^4$, $R^5$, A, n and m are defined as indicated for the formula I, or alternatively functional groups can be present in the form of precursors which are later converted into the groups present in the compounds of the formula I, or functional groups are present in protected form, and in which X is a nucleophilically substitutable leaving group, with a guanidine or guanidine derivative of the formula IV

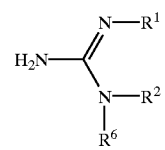

IV in which $R^1$, $R^2$ and $R^6$ are defined as indicated for the formula I, or alternatively functional groups can be present in the form of precursors which are later converted into the groups present in the compounds of the formula I, or functional groups are present in protected form.

The group COX in the formula III is preferably the carboxylic acid group COOH or an activated carboxylic acid derivative. X, for example, is hydroxyl or halogen, in particular chlorine or bromine, alkoxy, preferably methoxy or ethoxy, aryloxy, for example phenoxy, pentafluorophenoxy, phenylthio, methylthio, 2-pyridylthio or a radical of a nitrogen heterocycle bonded via a nitrogen atom, in particular of an azole, such as, for example, 1-imidazolyl. X can furthermore be, for example, (($C_1$–$C_4$)-alkyl)—O—CO—O— or tolylsulfonyloxy and the activated acid derivative can thus be a mixed anhydride.

If X is hydroxyl, i.e. if the guanidine of the formula IV is reacted with a carboxylic acid, then the carboxylic acid is expediently first activated. The activation can be carried out, for example, with dicyclohexylcarbodiimide (DCCI) or with O-((cyano(ethoxycarbonyl)-methylen)amino)-1,1,3,3-tetramethyluronium tetrafluoroborate (TOTU; König et al., Proc. 21st Europ. Peptide Symp. 1990 (Eds. Giralt, Andreu), Escom, Leiden 1991, p. 143) or other activating reagents customary in peptide chemistry.

Beside the free guanidines of the formula IV, guanidinium salts can also be employed in the reaction with the compounds of the formula III, from which the free guanidines are then prepared in situ or in a separate step by means of a base. The reaction of an activated carboxylic acid derivative of the formula III with the guanidine (derivate) of the formula IV is preferably carried out in a manner known per se in a protic or aprotic polar, but inert, organic solvent. In this case, methanol, isopropanol, tert-butanol, dimethylformamide or tetrahydrofuran at temperatures from 0° C. up to the boiling temperature of these solvents have proven suitable, for example, in the reaction of the methyl esters (X=methoxy) or of the ethyl esters (X=ethoxy) with the guanidines. The reactions of compounds of the type COX with salt-free guanidines are advantageously carried out in aprotic inert solvents such as dimethylformamide, tetrahydrofuran, dimethoxyethane or dioxane, if appropriate with addition of a base such as, for example, potassium tert-butoxide or sodium methoxide. However, water can also be used as a solvent in the reaction of compounds of the formula III with guanidines, for example when using a base such as sodium hdyroxide. If X is chlorine, the reaction is advantageously carried out with addition of an acid scavenger, for example of an added base or in the presence of excess guanidine (derivative) for binding the resulting hydrohalic acid. The reaction mixture is worked up and, if desired, the reaction product is then purified by the customary processes familiar to those skilled in the art.

Protective groups optionally still present in the products obtained from the compounds of the formulae III and IV are then removed by standard processes, for example tert-butyl ester groups are converted into the carboxylic acid groups by treatment with trifluoroacetic acid, benzyl groups are removed by hydrogenation or fluorenylmethoxycarbonyl groups are removed by secondary amines, and further reactions are carried out by standard processes, for example acylation reactions. If appropriate, conversion into physiologically tolerable salts or prodrugs can then be carried out by known processes.

The starting components of the formulae III and IV, which are linked to give the acylguanidine derivatives of the formula I, are commercially available or can be prepared by or analogously to processes described in the literature. The preparation of the starting components of the formula III is illustrated by way of example in the following schemes, the present invention not being restricted to these syntheses or these starting components. It does not cause any problems to those skilled in the art to carry out the modifications of the syntheses shown, which are necessary for the preparation of other compounds according to the invention.

Thus the carboxybenzaldehyde of the formula V can be reacted, for example in the presence of pyridine and piperidine, with the malonic acid ester salt of the formula VI to give the cinnamic acid derivative of the formula VII which, after hydrogenation, for example in the presence of palladium on carbon, to give the compound of the formula VII and activation of the carboxylic acid group, can be condensed with the 2,3-diaminopropionic acid derivative of the formula IX to give the compound of the formula X (Scheme 1). The condensation can be carried out, for example, in the presence of TOTU or another customary activating agent for carboxylic acids. In the formula X, Z is the benzyloxycarbonyl group, but instead of Z other groups can be present on the nitrogen atom which either only temporarily protect the amino group in the 2-position or which can also be present in the compounds of the formula I according to the invention and can remain in the molecule. Likewise, instead of the tert-butyl ester, other esters can be present which either only temporarily protect the acid group or which can also be present in the compounds of the formula I according to the invention and can remain in the molecule. Compounds analogous to the compound of the formula VII can also be obtained by other processes for the conversion of a carbonyl group into an alkene, for example by a Wittig reaction.

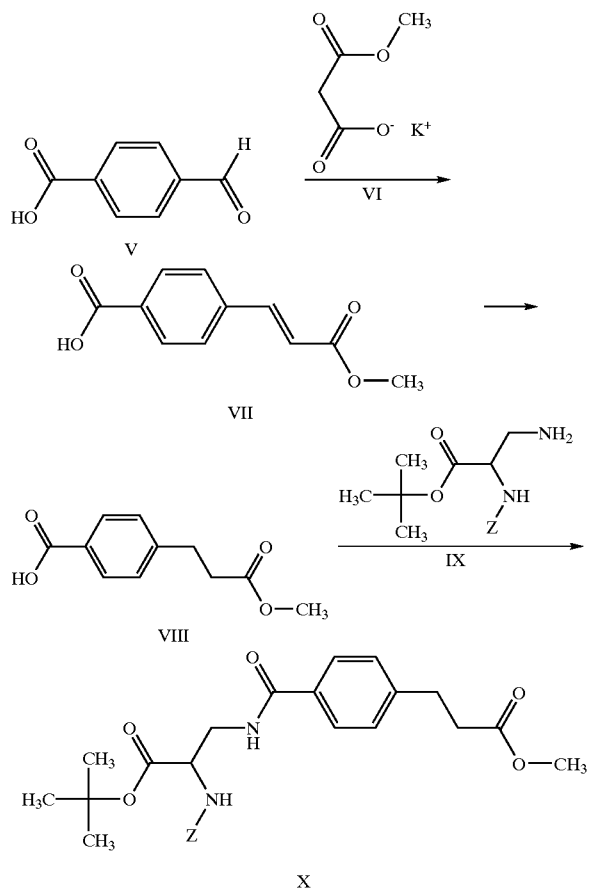

Scheme 1

The p-hydroxybenzoic acid of the formula XI can be condensed with the 2,3-diaminopropionic acid derivative of the formula IX to give the compound of the formula XII, the above explanations applying for the compound of the formula IX and the condensation. The compound of the formula XII can be alkylated with halocarboxylic acid derivatives under standard conditions, for example with the bromoacetic acid ester of the formula XIII to give the compound of the formula XIV (Scheme 2). p-Aminobenzoic acid and p-mercaptobenzoic acid can be reacted correspondingly.

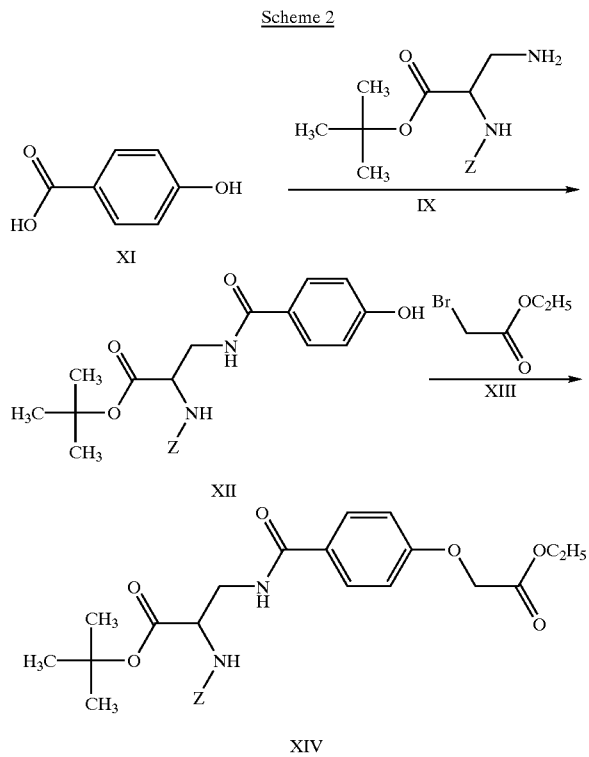

The tyrosine derivative of the formula XV can be alkylated under standard conditions with halocarboxylic acid derivatives, for example with the bromobutyric acid ester of the formula XVI to give the compound of the formula XVII (Scheme 3). In the formula XV, Z is the benzyloxycarbonyl group, but instead of Z other groups can be present on the nitrogen atom, which either only temporarily protect the amino group or which can also be present in the compounds of the formula I according to the invention and can remain in the molecule. Likewise, instead of the tert-butyl ester, other esters can be present which either only temporarily protect the acid group or which can also be present in the compounds of the formula I according to the invention and can remain in the molecule. Analogs of the compounds of the formula XVII can be prepared correspondingly or analogously to the above preparation processes.

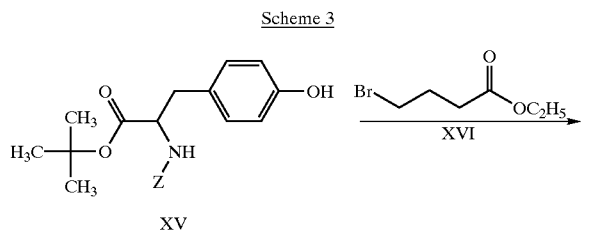

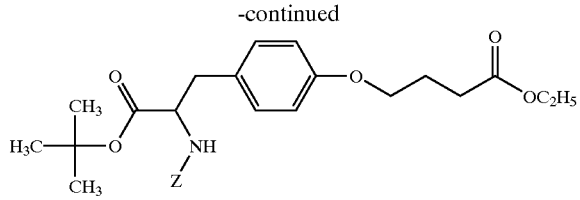

The compounds of the formulae X, XIV and XVII are examples of compounds of the formula III in which X is methoxy or ethoxy. These compounds and analogous compounds which are obtained from the syntheses described above containing a group which is an activated carboxylic acid derivative can be reacted directly with the compounds of the formula IV. The compounds obtained in the above syntheses, however, can also first be converted under standard conditions by cleavage of the methyl ester group or ethyl ester group or another ester group present in the position concerned in the compounds of the formulae X, XIV and XVII into the corresponding carboxylic acids, which are then reacted with the guanidines of the formula IV after in situ activation, for example with TOTU or DCCl, or after conversion into an activated carboxylic acid derivative. If, as activated acid derivatives, it is intended to prepare, for example, the carboxylic acid chlorides (formula III, X=Cl), this can be carried out, for example, using thionyl chloride. If it is intended to prepare, for example, the methyl esters (X=methoxy) from the carboxylic acids, this can be carried out by treating with gaseous hydrogen chloride in methanol. Other activated acid derivatives can be prepared in a manner known per se from the carboxylic acid chlorides or directly from the carboxylic acids on which they are based (X=OH), for example the imidazolides (X=1-imidazolyl) by treating the acids with carbonyldiimidazole (cf. Staab, Angew. Chem. Int. Ed. Engl. 1, 351–367 (1962)) or the mixed anhydrides, for example by reaction with chloroformic acid esters such as ethyl chloroformate or with tosyl chloride in the presence of amines such as triethylamine in an inert solvent. A number of suitable methods for the preparation of activated carboxylic acid derivatives are indicated with details of source literature in J. March, Advanced Organic Chemistry, Third Edition, John Wiley & Sons, 1985, p. 350.

The compounds of the formula I are valuable pharmaceutical active ingredients which are suitable, for example, for the therapy and prophylaxis of bone disorders, tumor diseases or cardiovascular disorders. The compounds of the formula I and their physiologically tolerable salts and their prodrugs can be administered to animals, preferably to mammals, and in particular to humans as pharmaceuticals for therapy or prophylaxis. They can be administered on their own, in mixtures with one another or in the form of pharmaceutical preparations which permit enteral or parenteral administration and which contain, in addition to customary pharmaceutically innocuous carriers and/or additives, an efficacious dose of at least one compound of the formula I and/or its physiologically tolerable salts and/or its prodrugs as active constituent.

The present invention therefore also relates to the compounds of the formula I and/or their physiologically tolerable salts and/or their prodrugs for use as pharmaceuticals, to the use of the compounds of the formula I and/or their physiologically tolerable salts and/or their prodrugs for the production of pharmaceuticals for the therapy and prophylaxis of the diseases mentioned above or below, for example for the therapy and prophylaxis of bone disorders or tumor diseases, and also to the use of the compounds of the formula I and/or their physiologically tolerable salts and/or their prodrugs for the therapy and prophylaxis of these diseases. The present invention furthermore relates to pharmaceutical preparations which contain an efficacious amount of at least one compound of the formula I and/or its physiologically tolerable salts and/or its prodrugs together with a customary pharmaceutically innocuous carrier.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously in the form of injection solutions or infusion solutions, microcapsules, implants or rods, or percutaneously or topical, for example in the form of ointments, solutions or tinctures, or in other ways, for example in the form of aerosols or nasal sprays.

The pharmaceutical preparations according to the invention are prepared in a manner known per se, one or more pharmaceutically inert inorganic and/or organic carriers being used in addition to the compound(s) of the formula I and/or its (their) physiologically tolerable salts and/or its (their) prodrugs. For the production of pills, tablets, coated tablets and hard gelatin capsules, it is possible to use, for example, lactose, corn starch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain approximately 0.5 to 90% by weight of the compound(s) of the formula I and/or its (their) physiologically tolerable salts and/or its (their) prodrugs. The amount of the active ingredient(s) of the formula I and/or its (their) physiologically tolerable salts and/or its (their) prodrugs in the pharmaceutical preparations normally is 0.2 to 500 mg, preferably 1 to 200 mg.

In addition to the active ingredients and carriers, the pharmaceutical preparations can additionally contain one or more additives, such as, for example, fillers, disintegrants, binders, lubricants, wetting agents, stabilizers, emulsifiers, preservatives, sweeteners, colorants, flavorings or aromatizers, thickeners, diluents, buffer substances, and also solvents or solubilizers or agents for achieving a depot effect, and also salts for altering the osmotic pressure, coating agents or antioxidants. They can also contain two or more compounds of the formula I and/or their physiologically tolerable salts and/or their prodrugs. Furthermore, in addition to at least one compound of the formula I and/or its physiologically tolerable salts and/or its prodrugs, they can also contain one or more other therapeutically or prophylactically active ingredients.

The compounds of the formula I are antagonists of the vitronectin receptor and have, for example, the ability to inhibit the binding of osteoclasts to the bone surface and thereby bone resorption by osteoclasts. The action of the compounds of the formula I can be demonstrated, for example, in an assay in which the inhibition of the binding of vitronectin to cells which contain the vitronectin receptor is determined. Details of such an assay are given below. As vitronectin receptor antagonists, the compounds of the formula I and their physiologically tolerable salts and their prodrugs are generally suitable for the therapy and prophylaxis of diseases which are based on the interaction between vitronectin receptors and their ligands in cell-cell interaction processes or cell-matrix interaction processes, or which can be influenced by an inhibition of interactions of this type, or for their prevention, alleviation or cure an inhibition of interactions of this type is desired. As explained at the beginning, such interactions, for example, play a part in bone resorption, in angiogenesis or in the proliferation of cells of the vascular smooth musculature. The compounds of the formula I and their physiologically tolerable salts and their prodrugs are therefore suitable, for example, for the alleviation or cure of diseases which are caused at least partially by an undesired extent of bone resorption, angiogenesis or proliferation of cells of the vascular smooth musculature.

Bone diseases for whose treatment and prevention the compounds of the formula I according to the invention can be employed are especially osteoporosis, hypercalcemia, osteopenia, for example caused by metastases, dental disorders, hyperparathyroidism, periarticular erosions in rheumatoid arthritis and Paget's disease. In addition, the compounds of the formula I can be used for the alleviation, avoidance or therapy of bone disorders which are caused by a glucocorticoid, steroid or corticosteroid therapy or by a lack of sex hormone(s). All these disorders are characterized by bone loss, which is based on the inequilibrium between bone formation and bone destruction and which can be favorably influenced by the inhibition of bone resorption by osteoclasts. The compounds of the formula I and/or their physiologically tolerable salts and/or their prodrugs can also favorably be used as inhibitor of bone resorption, for example in the therapy or prophylaxis of osteoporosis, in combination with conventional osteoporosis treatments, for example in combination with bisphosphonates, estrogens, estrogen/progesterone, estrogen agonists/antagonists, calcitonin, vitamin D analogues, parathyroid hormone, growth hormone secretagogues, or sodium fluoride. Administration of the compounds of the formula I and/or their physiologically tolerable salts and/or their prodrugs and of other active ingredients effective in the treatment or prophylaxis of osteoporosis like those listed before can take place simultaneously or sequentially, in any order, and jointly or separately. For use in such a combination treatment or prophylaxis the compounds of the formula I and/or their physiologically tolerable salts and/or their prodrugs and one or more other active ingredients like those listed before can together be present in a single pharmaceutical preparation, for example tablets or granules, or can be present in two or more separate pharmaceutical preparations which can be contained in a single package or in two or more separate packages. The use of the compounds of the formula I and/or their physiologically tolerable salts and/or their prodrugs in such a combination therapy or prophylaxis and their use in the production of pharmaceuticals for such a combination therapy or prophylaxis are also covered by the present invention. The invention furthermore relates to pharmaceutical preparations which comprise efficacious amounts of at least one compound of the formula I and/or its physiologically tolerable salts and/or its prodrugs together with at least one other active ingredient effective in the treatment. or prophylaxis of osteoporosis or in the inhibition of bone resorption like those listed before, together with a customary pharmaceutically innocuous carrier. The above explanations on pharmaceutical preparations correspondingly apply to such pharmaceutical combination preparations. Apart from use as inhibitors of bone resorption by osteoclasts, the compounds of the formula I and their physiologically tolerable salts and their prodrugs are used as inhibitors of tumor growth and tumor metastasis, as antiinflammatories, for the therapy or prophylaxis of cardiovascular disorders such as arteriosclerosis or restenosis, or for the therapy or prophylaxis of nephropathies or retinopathies, such as, for example, diabetic retinopathy. As inhibitors of tumor growth or tumor metastasis the compounds of the formula I and/or their physiologically tolerable salts and/or their prodrugs can also favorably be used in combination with conventional cancer therapy. Examples of conventional cancer therapy are given in Bertino (Editor), Encyclopedia of Cancer, Academic Press, 1997. All the above statements relating to the use of the compounds of formula I in combination with conventional osteoporosis therapy like, for example, possible modes of administration and pharmaceutical combination preparations, correspondingly apply to the use of the compounds of formula I in combination with conventional cancer therapy.

When using the compounds of the formula I, the dose can vary within wide limits and, as is customary, is to be suited to the individual conditions in each individual case. It depends, for example, on the compound employed which can be physiologically active by itself or can be a prodrug that is first metabolically activated, or on the nature and severity of the disease to be treated, or on whether an acute or chronic condition is treated or whether prophylaxis is carried out. In the case of oral administration, the daily dose is in general 0.01 to 100 mg/kg, preferably 0.1 to 50 mg/kg, in particular 0.1 to 5 mg/kg, for example 0.3 to 0.5 mg/kg, to achieve effective results in an adult weighing about 75 kg (in each case in mg per kg of body weight). Also in the case of intravenous administration the daily dose is in general approximately 0.01 to 100 mg/kg, preferably 0.05 to 10 mg/kg (in each case per kg of body weight). The daily dose can be divided, in particular in the case of the administration of relatively large amounts, into several, for example 2, 3 or 4, part administrations. If appropriate, depending on individual behavior, it may be necessary to deviate upwards or downwards from the daily dose indicated.

Apart from use as pharmaceutical active ingredients, the compounds of the formula I can also be used as vehicles or carriers of active ingredients in order to transport the active ingredient specifically to the site of action (=drug targeting; see, for example, Targeted Drug Delivery, R. C. Juliano, Handbook of Experimental Pharmacology, Vol. 100, Ed. Born, G. V. R. et al., Springer Verlag). The active ingredients to be transported are in particular those which can be used for the treatment of the abovementioned diseases.

The compounds of the formula I and their salts can furthermore be employed for diagnostic purposes, for example in in vitro diagnoses of cell or tissue samples, and as auxiliaries in biochemical investigations in which blocking of the vitronectin receptor or influencing of cell-cell or cell-matrix interactions is desired. They can furthermore be used as intermediates for the preparation of other compounds, in particular of other pharmaceutical active ingredients, which are obtainable from the compounds of the formula I, for example by modification or introduction of substituents or functional groups.

EXAMPLES

The products were identified via mass spectra (MS) and/or NMR spectra. Compounds which were purified by chromatography using an eluent which contained, for example, acetic acid or trifluoroacetic acid, and were then freeze-dried, or in which in the last synthesis step, for example, trifluoroacetic acid was employed to remove a tert-butyl protective group, in some cases still contained, depending on how the freeze-drying was carried out, the acid originating from the eluent or the last synthesis step and were obtained partially or completely in the form of a salt of the acid used, for example in the form of the acetic acid salt or trifluoroacetic acid salt.

Example 1

(2S)-2-Benzyloxycarbonylamino-3-(4-(3-( 1,4,5,6-tetrahydropyrimidin-2-ylcarbamoyl)propyloxy)phenyl)propionic Acid

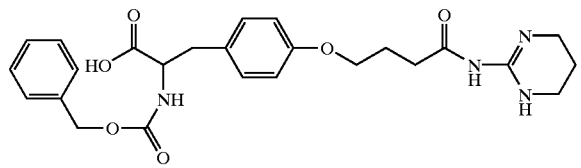

a) tert-Butyl (2S)-2-Benzyloxycarbonylamino-3-(4-(3-ethoxycarbonylpropyloxy)phenyl)propionate 7.42 g (0.02 mol) of N-benzyloxycarbonyl-L-tyrosine tert-butyl ester were refluxed for 6 h together with 9.77 g(0.03 mol) of cesium carbonate and 3.9 g (0.02 mol) of ethyl 4-bromo-butyrate in about 60 ml of acetone. After cooling the reaction mixture, the solvent was removed in vacuo. The residue was partitioned between ethyl acetate and water (1/1). After separation of the phases, the organic phase was washed two times each with water and saturated sodium chloride solution, dried over sodium sulfate and concentrated in vacuo. The oily crude product was purified by flash chromatography on silica gel (dichloromethane/acetonitrile 25/1). Yield: 9.4 g (97%) of viscous oil. $R_f$=0.36 (silica gel, dichloromethane/methanol 9911).

b) tert-Butyl (2S)-2Benzyloxycarbonylamino-3-(4-(3-(1,4,5,6-tetrahydropyrimidin-2-ylcarbamoyl)propyloxy)phenyl) propionate 6.72 g (0.06 mol) of potassium tert-butoxide were added to a solution of 8.13 g (0.06 mol) of 1-amino-1,4,5,6-tetrahydropyrimidine hydrochloride in 100 ml of absolute dimethylformamide. After stirring at room temperature for 30 min, 7.2 g (0.015 mol) of tert-butyl (2S)-2-benzyloxycarbonylamino-3-(4-(3-ethoxycarbonylpropyloxy)phenyl)propionate were added to this solution and it was stirred at room temperature for 12 h. After removal of the solvent in vacuo, the residue was treated with 300 ml of ethyl acetate and 100 ml of water, and the organic phase was separated off, washed two times with saturated sodium chloride solution, dried over sodium sulfate and concentrated. The crude product thus obtained was immediately chromatographed on silica gel (dichloromethane/methanol/glacial acetic acid 10015/1). 5.4 g (60.6%) of amorphous product were obtained.

c) (2S)-Benzyloxycarbonylamino-3-(4-(3-(1,4,5,6-tetrahydropyrimidin-2-ylcarbamoyl)propyloxy)phenyl) propionic Acid 5.4 g (0.009 mol) of tert-butyl (2S)-2-benzyloxycarbonylamino-3-(4-(3-(1,4,5,6-tetrahydropyrimidin-2-ylcarbamoyl)propyloxy)phenyl)propionate acetic acid salt were dissolved in 20 ml of trifluoroacetic acid/water (95/5) and the solution was stirred at room temperature for 30 min. The reaction solution was then concentrated in vacuo. The residue was dissolved in water and the solution was freeze-dried. Yield: 5.2 g (98%).

MS (ES$^+$): m/e=483.3 (M+H$^+$, 100%).

Example 2

(2S)-2-Benzyloxycarbonylamino-3-(4-(2-(1,4,5,6-tetrahydropyrimidin-2-ylcarbamoyl)ethyl)benzoylamino)propionic Acid

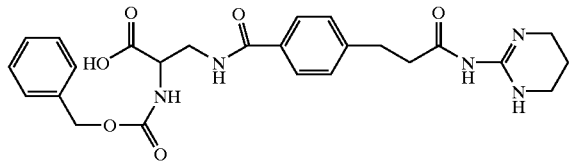

a) 4-(2-Methoxycarbonylvinyl)benzoic Acid 18.74 g (0.12 mol) of monomethyl malonate potassium salt were suspended in 18 ml of pyridine. 15.01 g (0.1 mol) of 4-carboxybenzaldehyde and 0.85 g (0.01 mol) of piperidine were added at room temperature with stirring. The mixture was refluxed until the evolution of $CO_2$ was complete (about 2 h), then a further 60 ml of pyridine were added and the mixture was stirred under reflux for a further 1 h. The reaction mixture was treated with stirring with 500 ml of ice and 110 ml of conc. hydrochloric acid. After addition was complete, the mixture was stirred for a further 20 min, and the product was filtered off with suction, washed with water and recrystallized from isopropanol. Yield: 12.85 g (62%).

$^1$H-NMR (200 MHz, d$^6$-DMSO): δ=3.75 (s, 3H, OCH$_3$); 6.76 (d, J=15Hz, 1H, C$\underline{H}$COOCH$_3$); 7.73 (d, J=15Hz, 1H, Ar—C$\underline{H}$); 7.84 (d, J=9Hz, 2H, Ar—H); 7.98 (d, J=9Hz, 2H, Ar—H); 13.11 (s, broad, 1H, COOH). MS (Cl$^+$): m/e=207.2 (M+H$^+$, 100%). HPLC: RP18, Nucleosil 300-5-C18, 250×4 mm; buffer A: H$_2$O, 0.1% trifluoroacetic acid (TFA); buffer B: acetonitrile (80% v/v)/H$_2$O (20% v/v), 0.1% TFA; gradient: first 5 min 90% buffer A/10% buffer B, then during 20 min to 90% buffer B, then 5 min 90% buffer B; flow rate 1 ml/min; Rt32 18.05 min.

b) 4-(2-Methoxycarbonylethyl)benzoic Acid 8 g (38.8 mmol) of 4-(2-methoxycarbonylvinyl)benzoic acid were suspended in 250 ml of dioxane and hydrogenated for 7 h at room temperature over Pd/C (10% strength) at 1 bar of hydrogen. The mixture was filtered and the solvent was removed in vacuo. Yield: 8.05 g (100%).

1H-NMR (200 MHz, d$_6$-DMSO): δ=2.67 (t, J=8Hz, 2H, C$\underline{H}_2$—COOCH$_3$); 2.93 (t, J=8Hz, 2H, Ar—C$\underline{H}_2$); 3.59 (s, 3H, OCH$_3$); 7.35 (d, 2H, Ar—H); 7.86 (d, J=9Hz, 2H, Ar—H); 12.80 (s, broad, 1H, COOH). MS (Cl$^+$): m/e=209.2 (M+H$^+$, 100%). HPLC:RP18, Nucleosil 300-5-C18, 250×4 mm; buffer A: H$_2$O, 0.1% TFA; buffer B: acetonitrile (80% v/v)/H$_2$O (20% v/v), 0.1% TFA; gradient: first 5 min 90% buffer A, 10% buffer B, then during 20 min to 90% buffer B, then 5 min 90 % buffer B; flow rate 1ml/min; R$_t$=17.03 min.

c) tert-Butyl (2S)-2-Benzyloxycarbonylamino-3-(4-(2-methoxycarbonylethyl)benzoylamino)propionate 354 mg (1.7 mmol) of 4-(2-methoxycarbonylethyl)benzoic acid and 500 mg (1.7 mmol) of tert-butyl (2S)-3-amino-2-benzyloxycarbonylaminopropionate were dissolved in 3 ml of dimethylformamide and treated with 557 mg (1.7 mmol) of O-((cyano-(ethoxycarbonyl)-methylidene)amino)-1,1,3,3-tetramethyluronium tetrafluoroborate (TOTU) and 204 mg (1.7 mmol) of diisopropylethylamine and the mixture was stirred at room temperature for 7 h at pH 7–8. The solvent was removed in vacuo, the residue was dissolved in ethyl acetate and the solution was washed three times each with KHSO$_4$ solution and NaHCO$_3$ solution until neutral. The organic phase was separated off and dried and the solvent was removed by distillation in vacuo. Yield: 770 mg (93%).

MS (ES$^+$): m/e=485.2 (M+H$^+$, 100%).

d) tert-Butyl (2S)-2-Benzyloxycarbonylamino-3-(4-(2-(1,4,5,6-tetrahydropyrimidin-2-ylcarbamoyl)ethyl)benzoylamino)propionate 1.25 g (9.2 mmol) of 2-amino-1,4,5,6-tetrahydropyrimidine hydrochloride and 1.03 g (9.2 mmol) of potassium tert-butoxide were dissolved in 3 ml of absolute dimethyl-formamide and stirred at room temperature for 30 min. 740 mg (1.53 mmol) of tert-butyl (2S)-2-benzyloxycarbonylamino-3,4-(2-methoxycarbonylethyl)benzoylamino)propionate in 1 ml of dimethylformamide were then added and the mixture was stirred at room temperature for 4 h. The pH was adjusted to 4 using glacial acetic acid, the solvent was removed in vacuo and the residue was chromatographed on silica gel using dichloromethane/methanol/glacial acetic acid/water (9/110.110.1). Yield: 190 mg (38%).

MS (ES$^+$): m/e=552.3 (M+H$^+$, 100%).

e) (2S)-2-Benzyloxycarbonylamino-3-(4-(2-(1,4,5,6-tetrahydropyrimidin-2-ylcarbamoyl)ethyl)benzoylamino)propionic Acid 1 90 mg (0.034 mmol) of tert-butyl (2S)-2-benzyloxycarbonylaminod-3-(4(2(1,4,5,6-tetrahydropyrimidin-2-ylcarbamoyl)ethy)benzoylamino)propionate were dissolved in 5 ml of 95% strength trifluoroactic acid and stirred at room temperature for 1 h. The trifluoroacetic acid was removed by distillation in vacuo and coevaporated with toluene, and the residue was dissolved in glacial acetic acid, diluted with water and freeze-dried. Yield: 170 mg (1.00%).

MS (ES$^+$): m/e=496.3 (M+H$^+$, 100%)

Example 3

(2S )-2-Benzyloxycarbonylamino-3-(4-((1,4,5,6-tetrahydropyrimidin-2-ylcarbamoyl)methyloxy)benzoylamino)propionic Acid

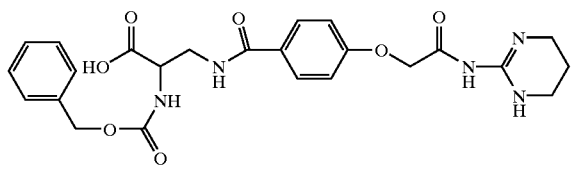

a) Benzyl 4-(Methoxycarbonylmethyloxy)benzoate 4.5 g (0.02 mol) of benzyl p-hydroxybenzoate were suspended in about 60 ml of acetone together with 9.7 g (0.03 mol) of cesium carbonate and treated with 2.3 ml (0.025 mol) of ethyl bromoacetate. The mixture was then refluxed until reaction was complete. For working-up, the reaction solution was filtered through a clarifying layer and the filtrate was concentrated to dryness. The residue was taken up in ethyl acetate and the mixture was washed three times each with 10% strength citric acid solution and saturated NaCl solution. The organic phase was dried over sodium sulfate, filtered and concentrated. The residue was recrystallized from diisopropyl ether/heptane. Yield: 5.5 g.

b) 4-(Methoxycarbonylmethyloxy)benzoic Acid 5 g of benzyl 4-(methoxycarbonylmethyloxy)benzoate were dissolved in methanol/ethyl acetate and hydrogenated in the presence of 600 mg of catalyst (Pd/C, 10% strength). After flushing with inert gas, the catalyst was filtered off and the filtrate was concentrated in vacuo. The residue was triturated with diisopropyl ether/heptane (9/1) and filtered off with suction. Yield: 3.3 g.

c) tert-Butyl (2S)-2-(Benzyloxycarbonylamino)-3-(4-(methoxycarbonylmethyloxy)benzoylamino)propionate 420 mg (0.002 mol) of 4-(methoxycarbonylmethyloxy) benzoic acid, 270 mg (0.002 mol) of 1-hydroxybenzotriazole and 588 mg (0.002 mol) of tert-butyl (2S)-3-amino-2-benzyloxycarbonylaminopropionate were dissolved in 5 ml of dimethylformamide. The solution was cooled to 0° C. and treated with 453 mg (0.0022 mol) of N,N'-dicyclohexylcarbodiimide and then stirred at 0° C. for 10 min and at room temperature for 2 h. For working-up, the urea was filtered off and the filtrate was concentrated to dryness. The pure compound was obtained by chromatography of the crude product on silica gel (dichloromethane/acetonitrile 20/1). Yield: 820 mg.

d) tert-Butyl (2S)-2-Benzyloxycarbonylamino-3-(4-((1,4,5,6-tetrahydropyrimidin-2-ylcarbamoyl)methyloxy)benzoylamino)propionate 438 mg of tert-butyl (2S)-2-(benzyloxycarbonylamino)-3-(4-(methoxycarbonylmethyloxy)benzoylamino) propionate, 606 mg of potassium tert-butoxide and 732 mg of 2-amino-1,4,5,6-tetrahydropyrimidine hydrochloride were dissolved in 10 ml of absolute dimethylformamide, and the solution was stirred at room temperature for 14 h and then concentrated to dryness in vacuo.

The residue was dissolved in ethyl acetate and the solution was extracted with water. The organic phase was dried and concentrated in vacuo, and the crude product was purified by chromatography on silica gel (dichloromethane/methanol 100/7.5). Yield: 370 mg.

e) (2S)-2-Benzyloxycarbonylamino-3-(4-((1,4, 5,6-tetrahydropyrimidin-2ylcarbamoyl)methyloxy)benzoylamino)propionic Acid 87 mg of the tert-butyl ester obtained in step d) were stirred at room temperature for 15 min in 2 ml of 95% strength trifluoroacetic acid. After concentrating in vacuo, the mixture was triturated with ether, and the residue was filtered off and dried. Yield: 79 mg.

MS (ES$^+$): m/e=498.2 (M+H)$^+$.

Example 4

Isopropyl (2S)-2-Benzyloxycarbonylamino-3-(4-(3-(1,4,5,6-tetrahydropyrimidin-2-ylcarbamoyl)propyloxy)phenyl)propionate Hydrochloride

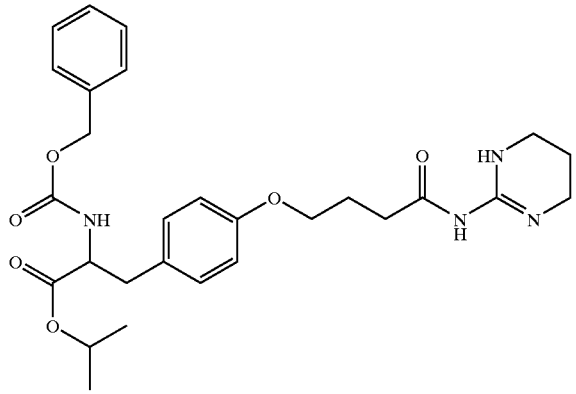

23.88 g (0.04 mol) of the compound of Example 1 (as trifluoroacetic acid salt) were suspended in 400 ml of isopropanol. To this suspension was added at −15° C. under an inert gas atmosphere a previously prepared solution of thionyl chloride in isopropanol (for the preparation of this solution 10.4 ml of thionyl chloride had been added dropwise at −10 to −15° C. and unter an inert gas atmosphere within 5 min to 160 ml of isopropanol and the mixture had been stirred at −10° C. for further 20 min). After completion of the addition the temperature rose within 30 min to room temperature. Then, the meanwhile clear solution was heated at 60° C. under stirring for 7 hours. Stirring was continued without heating overnight. By TLC control, the reaction exhibited to be completed. Solvents were removed by rotary destination in vacuo. The residue was suspended in 100 ml of isopropanol and the isopropanol was removed in vacuo. The solid residue was triturated with diethylether and separated by suction filtration. The raw product was suspended in 120 ml of isopropanol, heated to reflux with 2.4 g of charcoal and filtered. After cooling, the colourless product was separated by filtration. Yield: 16.2 g of an off-white solid.

MS (ES$^+$): m/e=525 (M+H$^+$, 100%). Elemental analysis: calc. C 59.9% H 6.6% N 10.0% Cl 6.3%; found C 59.3% H 6.7% N 10.0% Cl 6.6%; $^1$H-NMR (200 MHz, d$_6$-DMSO): δ=1.1 (dd, 6H, J=7Hz), 1.8, 1.95 and 2.5 (m, each 2H), 2.85 (m, 2H), 3.35 (t, 4H, J=3–4Hz), 3.95 (t, 2H, J=3–4Hz), 4.15 (m, 1H), 4.9 (sep, 1H, J=7Hz), 5.0 (s, 2H,), 6.9 and 7.1 (d, each 2H, J=7Hz), 7.3 (m, 5H), 7.7 (d, 1H, J=7Hz).

Example 5

Ethyl (2S)-2-Benzyloxycarbonylamino-3-(4-(3-(1,4,5,6-tetrahydropyrimidin-2-ylcarbamoyl)propyloxy)phenyl)propionate Hydrochloride

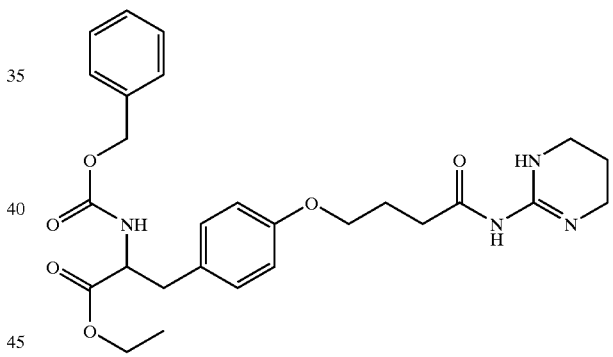

0.14 ml (1.15 eq.) of thionyl chloride were added at −10° C. to 5 ml of ethanol and stirred for 10 min at this temperature. Then 1 g (1.66 mmol) of the compound of Example 1 were added as a suspension in 10 ml of ethanol. Under stirring, the mixture was warmed to room temperature and stirred for further 5 hours. The solution which had meanwhile become clear, was evaporated in vacuo, the residue was dissolved in water and, after filtration, subjected to lyophilization. Yield: 0.85 g of a colourless, amorphous solid. MS (ES$^+$): m/e=511 (M+H$^+$, 100%).

Example 6

(2S)-2-Benzyloxycarbonylamino-3-(4-(3-(4,5-dihydro-1H-imidazol-2-ylcarbamoyl)propyloxy)phenyl)propionic Acid

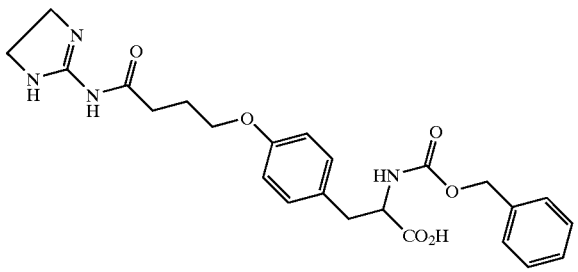

a) tert-Butyl (2S)-2-Benzyloxycarbonylamino-3(4-(3-(4,5-dihydro-1H-imidazol-2-ylcarbamoyl)propyloxy)phenyl) propionate 340 mg of 4,5-dihydro-1H-imidazol-2-ylamine, 13.6 mg of imidazole and 26.8 mg of lithium iodide were added to a solution of 970 mg of tert-butyl (2S)-2-benzyloxycarbonylamino-3-(4-(3-ethoxycarbonylpropyl-oxy)phenyl) propionate (Example 1a) in 5 ml of absolute dimethylformamide. The solution was stirred at 40° C. for 4 hours, an additional 170 mg of 4,5-dihydro-1H-imidazol-2-ylamine were added and the solution stirred at 55° C. for further 3 hours. After removal of the solvent in vacuo, the residue was treated with ethyl acetate, filtered, extracted with 10% strength aqueous $KHCO_3$ solution, dried over $MgSO_4$, filtered, concentrated in vacuo and precipitated with diisopropyl ether. The crude product was purified by silica gel chromatography (dichloromethane/methanol/glacial acetic acid 90/10/1). 250 mg of an amorphous product were obtained.

MS ($ES^+$): m/e=525.2 (M+H, 100%).

b) (2S)-2-Benzyloxycarbonylamino-3-(4-(3-(4,5-dihydro-1H-imidazol-2-ylcarbamoyl)propyloxy)phenyl)propionic Acid 200 mg of tert-butyl (2S)-2-benzyloxycarbonylamino-3-(4-(3-(4,5-dihydro-1H-imidazol-2-ylcarbamoyl)-propoxy) phenyl)propionate were dissolved in 5 ml of trifluoroacetic acid/water (95/5) and the solution was stirred at room temperature for 15 min. The reaction solution was then concentrated in vacuo. The residue was dissolved in water and the solution was freeze-dried. Yield: 100%.

MS ($ES^+$): m/e=469.2 ($M+H^+$, 100%).

Pharmacological Testing

The inhibition of bone resorption by the compounds according to the invention can be determined, for example, with the aid of an osteoclast resorption test ("PIT ASSAY"), for example analogously to WO-A-95/132710.

The inhibitory action of the compounds according to the invention against the vitronectin receptor $\alpha_v\beta_3$ can be determined, for example, as described below.

Test for the measurement of the inhibition of binding of 293 cells to human vitronectin (Vn/293 cell test)

1. Purification of Human Vitronectin

Human vitronectin is isolated from human plasma and purified by affinity chromatography according to the method of Yatohyo et al., Cell Structure and Function, 1988, 23, 281–292.

2. Cell Test 293 cells, a human embryonic kidney cell line, which are cotransfected with DNA sequences for the $\alpha_v$ and $\beta_3$ subunits of the vitronectin receptor $\alpha_v\beta_3$, are selected for a high rate of expression (>500,000 $\alpha_v\beta_3$ receptors/cell) according to the FACS method. The selected cells are cultured and sorted again by means of FACS in order to obtain a stable cell line (15 D) with expression rates >1,000,000 copies of $\alpha_v\beta_3$ per cell.

A Linbro 96-well tissue culture plate with a flat bottom is coated overnight at 4° C. with human vitronectin (0.01 mg/ml, 0.05 ml/well) in phosphate-buffered saline solution (PBS) and then blocked with 0.5% strength BSA (bovine serum albumin). Solutions of the test substances from $10^{-10}$ mol/l to $2\times10^{-3}$ mol/l in glucose-containing DMEM medium are prepared and 0.05 ml/well of the solution are added to the plate in each case. The cells which express high levels of $\alpha_v\beta_3$ (for example 15 D) are suspended in glucose-containing DMEM medium and the suspension is adjusted to a content of 25,000 cells/0.05 ml of medium. 0.05 ml of this cell suspension is added to each well and the plate is incubated at 37° C. for 90 min. The plate is washed three times with warm PBS in order to remove unbound cells. The bound cells are lyzed in citrate buffer (25 mM, pH 5.0) which contains 0.25% Triton X-100. The hexoseamidase substrate p-nitrophenyl-N-acetyl-β-D-glucosaminide is then added and the plate is incubated at 37° C. for 90 min. The reaction is stopped with a glycine (50 mM)/EDTA (5 mM) buffer (pH 10.4) and the absorption of each well is measured at 405–650 nm. The data are analyzed according to standard processes.

The following test results were obtained:

| Compound | Vn/293 cell test $IC_{50}$ (μM) |
|---|---|
| Example 1 | 0.028 |
| Example 2 | 0.017 |
| Example 3 | 1.35 |
| Example 6 | 0.032 |

What is claimed is:
1. A compound of formula I

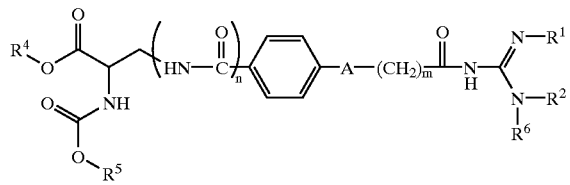

in which:

$R^1$ and $R^2$ together are a saturated or unsaturated bivalent $(C_2–C_9)$-alkylene radical and thereby form a ring, which is unsubstituted or is substituted by one or more groups selected from the group consisting of halogen, $(C_1–C_6)$-alkyl, $(C_1–C_6)$-alkoxy, $(C_6–C_{14})$-aryl, $(C_6–C_{14})$-aryl-$(C_1–C_6)$-alkyl-, $(C_5–C_{14})$-heteroaryl, $(C_5–C_{14})$-heteroaryl-$(C_1–C_6)$-alkyl-, $(C_3–C_{12})$-cycloalkyl, $(C_3–C_{12})$-cycloalkyl-$(C_1–C_6)$-alkyl- and oxo, where a 5-membered to 7-membered saturated or unsaturated ring may be fused to adjacent carbon atoms of the $(C_2–C_9)$ alkylene radical, thereby forming a bicyclic structure and is unsubstituted or is substituted by $R^3$, wherein said 5-membered to 7-membered saturated or unsaturated ring is a carbocyclic ring or a heterocyclic ring containing one or two nitrogen atoms;

$R^3$ is $(C_1–C_8)$-alkyl, $(C_1–C_8)$-alkoxy, $(C_5–C_{14})$-aryl, $(C_5–C_{14})$-aryl$(C_1–C_4)$-alkyl-, halogen, trifluoromethyl, hydroxyl, nitro, or amino;

$R^4$ is hydrogen, $(C_1–C_6)$-alkyl-CO—O—$(C_1–C_4)$-alkyl- or $(C_1–C_6)$-alkyl, which is unsubstituted or substituted by a radical selected from the group consisting of hydroxyl, $(C_1–C_4)$-alkoxy, $(C_1–C_4)$-alkyl-S(O)$_2$—, $NR^7R^{7'}$ and $N^+R^7$, $R^7R^{7''}Q^{31}$, wherein $R^7$, $R^{7'}$ and $R^{7''}$ independently of one another are hydrogen, $(C_1-C_6)$-alkyl, $(C_5-C_{14})$-aryl or $(C_5-C_{14})$-aryl-$(C_1-C_6)$-alkyl- and Q$^-$ is a physiologically tolerable anion, or in which $R^4$ is one of the radicals

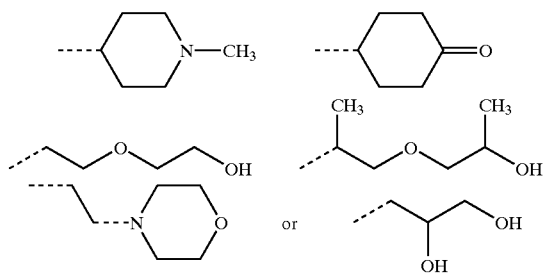

in which the bonds, via which the radicals are bonded, are indicated by dashed lines;

$R^5$ is $(C_1-C_6)$-alkyl, $(C_6-C_{14})$-aryl-$(C_1-C_6)$-alkyl- or $(C_5-C_{14})$-heteroaryl-$(C_1-C_6)$-alkyl-, where the aryl radical or the heteroaryl radical is unsubstituted or is substituted by one, two or three radicals $R^3$;

$R^6$ is hydrogen, $(C_1-C_6)$-alkyl-O—CO—, hydroxyl, $(C_1-C_6)$-alkyl-O—CO—O— or nitro;

A is CH2, O, S or NH;

m is 1, 2 or 3;

n is 0 or 1;

in all its stereoisomeric forms and mixtures thereof in all ratios, or its physiologically tolerable salt.

2. A compound of the formula I as claimed in claim 1, in which $R^1$ and $R^2$ together are a saturated or unsaturated bivalent $(C_2-C_5)$-alkylene radical, where the $(C_2-C_5)$-alkylene radical is unsubstituted or is substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_4)$-heteroaryl, $(C_5-C_{14})$-heteroaryl-$(C_1-C_5)$-alkyl-, $(C_3-O_{12})$-cycloalkyl, $(C_3-C_{12})$-cycloalkyl-$(C_1-C_6)$-alkyl- and oxo, and where a 5-membered to 7-membered saturated or unsaturated ring which is unsubstituted or substituted by $R^3$, and which is a carbocyclic ring or heterocyclic ring containing one or two ring nitrogen atoms, can be fused to a carbon-carbon bond in the $(C_2-C_5)$-alkylene radical;

$R^3$ is $(C_{1-C4})$-alkyl or $(C_1-C_4)$-alkoxy;

$R^4$ is hydrogen or $(C_1-C_6)$-alkyl which is unsubstituted or is substituted by a radical from the group consisting of $(C_1-C_4)$-alkoxy, $C_1-C_4$-alkyl-S(O)$_2$— and NR$^7$R', where $R^7$ and R' independently of one another are hydrogen or $(C_1-C_4)$-alkyl;

$R^5$ is $(C_1-C_8)$-alkyl or a radical of the formula II

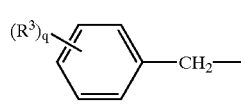

in which q is 0 or 1 and the radical $R^3$ can be located in any desired position of the phenyl radical;

$R^6$ is hydrogen or $(C_1-C_6)$-alkyl-O—CO—;

A is CH$_2$ or O;

m is 1, 2 or 3;

n is 0 or 1;

in all its stereoisoeric forms and mixtures thereof in all ratios, or its physiologically tolerable salt.

3. A compound of the formula I as claimed in claim 1 or 2, in which $R^1$ and $R^2$ together are a saturated or unsaturated bivalent $(C_2-C_4)$-alkylene radical, where the $(C_2-C_4)$-alkylene radical is unsubstituted or is substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl, $(C_3-C_{12})$-cycloalkyl-$(C_1-C_6)$-alkyl- and oxo, and where a 5-membered to 7-membered saturated or unsaturated ring which is unsubstituted or is substituted by $R^3$, and which is a carbocyclic ring or heterocyclic ring containing one or two ring nitrogen atoms, can be fused to a carbon-carbon bond in the $(C_2-C_4)$-alkylene radical;

$R^3$ is $(C_1-C_4)$-alkyl or $(C_1-C_4)$-alkoxy;

$R^4$ is hydrogen or $(C_1-C_6)$-alkyl;

$R^5$ is $(C_1-C_4)$-alkyl or a radical of the formula II

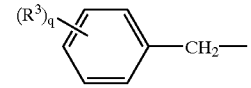

in which q is 0 or 1 and the radical $R^3$ can be located in any desired position of the phenyl radical;

$R^6$ is hydrogen or $(C_1-C_4)$-alkyl-O—CO—;

A is CH$_2$ or O;

m is 1, 2 or 3;

n is 0 or 1;

in all its stereoisomeric forms and mixtures thereof in all ratios, or its physiologically tolerable salt.

4. A compound of the formula I as claimed in one or more of claims 1 to 3, in which $R^1$ and $R^2$ together are a saturated or unsaturated bivalent $(C_2-C_3)$-alkylene radical, where the $(C_2-C_3)$-alkylene radical is unsubstituted or is substituted by a radical from the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl-, $(C_5-C_{14})$-heteroaryl, $(C_5-C_{14})$-heteroaryl-$(C_1-C_6)$-alkyl-, $(C_3-C_{12})$-cycloalkyl ($_3-C_{12}$)-cycloalkyl-$(C_1-C_6)$-alkyl- and oxo, and where a 5-membered to 7-membered saturated or unsaturated ring which is unsubstituted or is substituted by $R^3$, and which is a carbocyclic ring or heterocyclic ring containing one or two ring nitrogen atoms, can be fused to a carbon-carbon bond in the $(C_2-C_3)$-alkylene radical;

$R^3$ is $(C_1-C_4)$-alkyl or $(C_1-C_4)$-alkoxy;

$R^4$ is hydrogen or $(C_1-C_4)$-alkyl;

$R^5$ is $(C_1-C_4)$-alkyl or a radical of the formula II

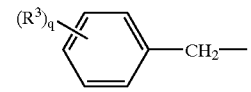

in which q is 0 or 1 and the radical $R^3$ can be located in any desired position of the phenyl radical;

$R^6$ is hydrogen or $(C_1-C_4)$-alkyl-O—CO—;

A is CH$_2$;

m is 1;

n is 1;

in all its stereoisomeric forms and mixtures thereof in all ratios, or its physiologically tolerable salt.

5. A compound of the formula I as claimed in one or more of claims 1 to 3, in which $R^1$ and $R^2$ together are a saturated or unsaturated bivalent ($C_2$–$C_3$)-alkylene radical, where the ($C_2$–$C_3$)-alkylene radical is unsubstituted or is substituted by a radical from the group consisting of halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl-, ($C_5$–$C_{14}$)-heteroaryl, ($C_5$–$C_{14}$)-heteroaryl-($C_1$–$C_6$)-alkyl-, ($C_3$–$C_{12}$)-cycloalkyl, ($C_3$–$C_{12}$)-cycloalkyl-($C_1$–$C_6$)-alkyl- and oxo, and where a 5-membered to 7-membered saturated or unsaturated ring which is unsubstituted or is substituted by $R^3$, and which is a carbocyclic ring or heterocyclic ring containing one or two ring nitrogen atoms, can be fused to a carbon-carbon bond in the ($C_2$–$C_3$)-alkylene radical;

$R^3$ is ($C_1$–$C_4$)-alkyl or ($C_1$–$C_4$)-alkoxy;

$R^4$ is hydrogen or ($C_1$–$C_4$)-alkyl;

$R^5$ is ($C_1$–$C_4$)-alkyl or a radical of the formula II

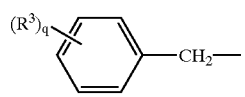

II in which q is 0 or 1 and the radical $R^3$ can be located in any desired position of the phenyl radical;

$R^6$ is hydrogen or ($C_1$–$C_4$)-alkyl-O—CO—;

A is oxygen;

m is 1;

n is 1;

in all its stereoisomeric forms and mixtures thereof in all ratios, or its physiologically tolerable salt.

6. A compound of the formula I as claimed in one or more of claims 1 to 3, in which $R^1$ and $R^2$ together are a saturated or unsaturated bivalent ($C_2$–$C_3$)-alkylene radical, where the ($C_2$–$C_3$)-alkylene radical is unsubstituted or is substituted by a radical from the group consisting of halogen, ($C_1$–$C_6$)-alkyl, ($C_1$–$C_6$)-alkoxy, ($C_6$–$C_{14}$)-aryl, ($C_6$–$C_{14}$)-aryl-($C_1$–$C_6$)-alkyl-, ($C_5$–$C_{14}$)-heteroaryl, ($C_5$–$C_{14}$)-heteroaryl-($C_1$–$C_6$)-alkyl-, ($C_3$–$C_{12}$)-cycloalkyl, ($C_3$–$C_{12}$)-cycloalkyl-($C_1$–$C_6$)-alkyl- and oxo, and where a 5-membered to 7-membered saturated or unsaturated ring which is unsubstituted or is substituted by $R^3$, and which is a carbocyclic ring or heterocyclic ring containing one or two ring nitrogen atoms, can be fused to a carbon-carbon bond in the ($C_2$–$C_3$)-alkylene radical;

$R^3$ is ($C_1$–$C_4$)-alkyl or ($C_1$–$C_4$)-alkoxy;

$R^4$ is hydrogen or ($C_1$–$C_4$)-alkyl;

$R^5$ is ($C_1$–$C_4$)-alkyl or a radical of the formula II

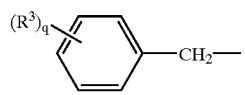

II in which q is 0 or 1 and the radical $R^3$ can be located in any desired position of the phenyl radical;

$R^6$ is hydrogen or ($C_1$–$C_4$)-alkyl-O—CO—;

A is oxygen;

m is 3;

n is 0;

in all its stereoisomeric forms and mixtures thereof in all ratios, or its physiologically tolerable salt.

7. A compound of the formula I as claimed in one or more of claims 1 to 6, in which $R^5$ is the unsubstituted benzyl radical, in all its stereoisomeric forms and mixtures thereof in all ratios, or its physiologically tolerable salt.

8. A compound of the formula I as claimed in one or more of claims 1 to 7, in which $R^1$ and $R^2$ together are a saturated bivalent ($C_2$–$C_3$)-alkylene radical which is unsubstituted;

$R^4$ is hydrogen or ($C_1$–$C_4$)-alkyl;

$R^5$ is unsubstituted benzyl;

$R^6$ is hydrogen;

A is oxygen;

m is 3;

n is 0;

in all their stereoisomeric forms and mixtures thereof in all ratios, or their physiologically tolerable salt.

9. (2S)-2-Benzyloxycarbonylamino-3-(4-(3-(1,4,5,6-tetrahydropyrimidin-2-ylcarbamoyl)propyloxy)phenyl) propionic acid or its physiologically tolerable salt.

10. (2S)-2-Benzyloxycarbonylamino-3-(4-(2-(1,4,5,6-tetrahydropyrimidin-2-ylcarbamoyl)ethyl)benzoylamino) propionic acid or its physiologically tolerable salt.

11. (2S)-2-Benzyloxycarbonylamino-3-(4-((1,4,5,6-tetrahydropyrimidin-2-ylcarbamoyl)methyloxy) benzoylamino)propionic acid or its physiologically tolerable salt.

12. (2S)-2-Benzyloxycarbonylamino-3-(4-(3-(4,5-dihydro-1H-imidazol-2-ylcarbamoyl)propyloxy)phenyl) propionic acid or its physiologically tolerable salt.

13. A process for the preparation of a compound of the formula I as claimed in one or more of claims 1 to 12 which comprises linking two or more fragments which can be derived retrosynthetically from the formula I.

14. The process as claimed in claim 13, wherein a carboxylic acid or a carboxylic acid derivative of the formula III

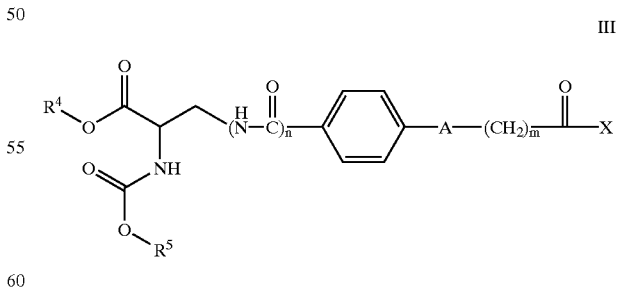

III in which $R^4$, $R^5$, A, n and m are defined as indicated in claims 1 to 12, or alternatively functional groups can be present in the form of precursors or in protected form, and X is a nucleophilically substitutable leaving group, is reacted with a guanidine or guanidine derivative of the formula IV

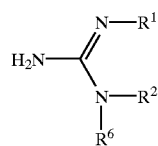

in which $R^1$, $R^2$ and $R^6$ are defined as indicated in claims 1 to 12, or alternatively functional groups can be present in the form of precursors or in protected form.

15. A pharmaceutical composition, comprising at least one compound of the formula I as claimed in one of claims 1 to 12 or its physiologically tolerable salt together with a pharmaceutically innocuous carrier.

16. A method of inhibiting a vitronectin receptor comprising contacting said vitronectin receptor with an inhibitory amount of a compound of formula I as claimed in one of claims 1 to 12.

17. A method for inhibiting bone resorption comprising administering to a patient in need thereof an inhibitory amount of a compound of formula I as claimed in one of claims 1 to 12 or its physiologically tolerable salt.

18. A method of treating osteoporosis comprising administering to a patient in need thereof an effective amount of a compound of formula I as claimed in one of claims 1 to 12 or its physiologically tolerable salt.

19. A method of treating tumor growth or tumor metastasis comprising administering to a patient in need thereof an effective amount of a compound of formula I as claimed in one of claims 1 to 12 or its physiologically tolerable salt.

20. A method of treating cardiovascular disorders, restenosis, arteriosclerosis, nephropathies or retinopathies comprising administering to a patient in need thereof an effective amount of a compound of formula I as claimed in one of claims 1 to 12 or its physiologically tolerable salt.

* * * * *